United States Patent
Renesto et al.

(10) Patent No.: US 8,219,193 B2
(45) Date of Patent: Jul. 10, 2012

(54) ACTIVE IMPLANTABLE MEDICAL DEVICE FOR CARDIAC RESYNCHRONIZATION WITH AUTOMATIC OPTIMIZATION OF ATRIOVENTRICULAR AND INTERVENTRICULAR DELAYS

(75) Inventors: Fabrizio Renesto, Borgofranco d'Ivrea (IT); Cyrille Casset, Saint Selve (FR)

(73) Assignee: Sorin CRM S.A.S., Clamart (FR)

( * ) Notice: Subject to any disclaimer, the term of this patent is extended or adjusted under 35 U.S.C. 154(b) by 80 days.

(21) Appl. No.: 12/906,844

(22) Filed: Oct. 18, 2010

(65) Prior Publication Data

US 2011/0093027 A1  Apr. 21, 2011

(30) Foreign Application Priority Data

Oct. 19, 2009 (FR) ...................... 09 57316

(51) Int. Cl.
*A61N 1/368* (2006.01)
(52) U.S. Cl. .......................... 607/9; 600/513
(58) Field of Classification Search ....... 607/9; 600/513
See application file for complete search history.

(56) References Cited

U.S. PATENT DOCUMENTS

| | | | |
|---|---|---|---|
| 6,556,866 B2 | 4/2003 | Dal Molin et al. | |
| 7,664,547 B2 | 2/2010 | Plicchi et al. | |
| 2004/0078060 A1* | 4/2004 | Ding et al. | 607/25 |
| 2005/0027320 A1 | 2/2005 | Nehls et al. | |
| 2005/0209649 A1 | 9/2005 | Ferek-Petric | |
| 2006/0293715 A1* | 12/2006 | Plicchi et al. | 607/9 |
| 2007/0179542 A1 | 8/2007 | Prakash et al. | |
| 2008/0249585 A1 | 10/2008 | Lippert et al. | |
| 2009/0157134 A1* | 6/2009 | Ziglio et al. | 607/9 |
| 2009/0209875 A1 | 8/2009 | Giorgis et al. | |

FOREIGN PATENT DOCUMENTS

| | | |
|---|---|---|
| EP | 1108446 | 6/2001 |
| EP | 1736203 | 12/2006 |
| EP | 1 977 784 | 10/2008 |
| EP | 2 092 885 | 8/2009 |
| WO | WO 2005/089866 | 9/2005 |

OTHER PUBLICATIONS

Foreign Search Report (Annexe Au Rapport De Recherche Preliminaire Relatif A La Demande De Brevet Francais No. FR0957316 FA 727588).
Jean-Marc Dupuis, et al., "Programming Optimal Atrioventricular Delay in Dual Chamber Pacing Using Peak Endocardial Acceleration", PACE, vol. 26, Part II, Jan. 2003.

* cited by examiner

*Primary Examiner* — Carl H Layno
*Assistant Examiner* — Yun Haeng Lee
(74) *Attorney, Agent, or Firm* — Orrick Herrington & Sutcliffe, LLP (57) ABSTRACT

An active implantable medical device for cardiac resynchronization with automatic optimization of atrioventricular and interventricular delays is disclosed. The device collects an endocardial acceleration signal EA and calculates the atrioventricular delay AVD and the interventricular delay VVD. The device isolate in the EA signal a component EA4 corresponding to the fourth EA peak and measure a temporal parameter related to a time interval between the detection of an atrial event (P/A) and the occurrence of the EA4 component. The device isolates an EA1 component corresponding to the first EA peak and measures a non-temporal parameter ($A_{PEA1}$) related to the peak amplitude or a signal energy of the EA1 component. The optimal AVD (AVDO) is determined by the temporal parameter related to the EA4 component, and is calculated for a plurality of different values of VVD to obtain a plurality of pairs of optimal values {AVDO, VVD}. The device selects one of these pairs of values based on the non-temporal parameter related to the EA1 component.

8 Claims, 5 Drawing Sheets

ACTIVE IMPLANTABLE MEDICAL DEVICE FOR CARDIAC RESYNCHRONIZATION WITH AUTOMATIC OPTIMIZATION OF ATRIOVENTRICULAR AND INTERVENTRICULAR DELAYS

This present application claims the benefit of French Application No. 09 57316 entitled "Active Implantable Medical Device For Cardiac Resynchronization With Automatic Optimization Of Atrioventricular And Interventricular Delays" and filed Oct. 19, 2009, which is hereby incorporated by reference in its entirety.

FIELD OF THE INVENTION

The present invention relates to "active implantable medical devices" as defined by the 20 Jun. 1990 Directive 90/385/EEC of the Council of the European Communities, and more particularly to devices that continuously monitor a patient's heart rhythm and deliver to the patient's heart, if necessary, electrical stimulation pulses to resynchronize the left and the right ventricles. This technique is often referred to as cardiac resynchronization therapy (CRT) or bi-ventricular pacing (BVP).

BACKGROUND

A patient in need of cardiac resynchronization can have an implanted device with electrodes to stimulate both ventricles. The device can continuously monitor the patient's heart rhythm and deliver if necessary to the patient's heart electrical impulses to stimulate both the left and right ventricles so as to resynchronize them.

The implanted device applies between the respective moments of stimulation of the left and right ventricles an "interventricular delay" (exchangeably referred to as "VVD" or "DVV") that can be adjusted to resynchronize the contraction of both ventricles towards optimizing the patient's hemodynamic status.

One of such known implantable devices is a CRT pacemaker disclosed in EP 1108446 A1 and its counterpart U.S. Pat. No. 6,556,866 (both assigned to Sorin CRM, previously known as ELA Medical) that applies between the two ventricular stimulations a variable VVD that can be adjusted to resynchronize the contractions of the ventricles with a fine optimization of the hemodynamic status of the patient.

A simultaneous stimulation of both ventricles is not always optimal, because it does not necessarily lead to a synchronous contraction of both ventricles. This is because, firstly, the conduction delays in the myocardium are not necessarily the same in the right and left ventricles, and may depend on multiple factors and, secondly, the location of the left ventricular lead, whether it is a lead inserted into the coronary sinus or an epicardial lead, can affect the detection of the ventricular contractions as well as the delay in stimulation. It is, therefore, desirable to establish a delay between the two stimuli, to adjust this delay to resynchronize the contractions of the ventricles, and to provide a fine optimization of hemodynamics. The VVD may be set to be zero, positive (the left ventricle is stimulated after the right ventricle), or negative (the right ventricle is stimulated after the left ventricle).

A known CRT device operates in a classical "double chamber" pacing mode in which the device monitors the ventricular activity after a spontaneous (i.e., a detection of an atrial P wave depolarization) or stimulated (i.e., application of an atrial pacing pulse A) atrial event. At the same time, the device starts to count a period called "atrioventricular delay" (exchangeably referred to as "AVD" or "DAV") such that if no spontaneous ventricular activity (i.e., an R wave) was detected before the end of the delay, the device triggers a stimulation of the ventricle (i.e., application of a ventricular pulse V).

Resynchronization therapy based on stimulation of both ventricles requires selection of operating parameters. These operating parameters are individualized to address myocardial contraction disorders (whether spontaneous or induced by a traditional stimulation) such as dilatation of the cardiac chambers, low ejection fraction, and excessive elongation of the QRS duration.

Some clinical studies have observed dramatic positive results for a patient who has congestive heart failure that did not effectively respond to conventional therapies with the precise adjustment of the operating parameters of CRT therapy according to the patient's condition and specific disorder.

These operating parameters are generally designated as a "stimulation configuration", a term combining the features related to the stimulation sites (i.e., the physical location of the electrodes and the choice of electrodes, in the case of multisite devices) and the sequence of stimulation (i.e., the order in which the stimulation pulses are applied to the heart on the different selected sites and the time interval between successive pulses).

It is also necessary to reassess these operating parameters after they are established and readjust them, if necessary. Indeed, one of the benefits provided by the CRT therapy is the capability of changing the original configuration and the stimulation setup in the long term.

One of the known techniques for adjusting the CRT stimulation parameters is an echocardiographic assessment that estimates the characteristic timings of the systole, in particular, the timing for the opening of the aortic valve. This procedure, typically implemented in hospitals and by skilled personnel, takes a long time, is expensive to implement, and cannot be applied as often as it would be useful or necessary without interfering with the patient's daily life, despite the expected beneficial effects.

Another difficulty inherent with an echocardiographic assessment is that it requires several successive test patterns of stimulation to determine an optimal AVD for each test pattern. The number of combinations to be tested is, therefore, important, but the assessment procedure involves a complicated, time-consuming, and difficult management and processing of the test results to determine an optimal AVD, therefore it is difficult to be applied as a routine and frequent procedure.

Moreover, even with a full implementation of these echocardiographic assessment procedures, approximately 30% of patients do not respond well to the CRT therapy. Even those 30% of the responding patients suffer serious negative consequences such as lower quality of life, increased hospitalizations related to heart failure, and a reduced life expectancy. Most of the studies now focus on treating this refractory patient population by experimenting with new stimulation configurations, and seeking to optimize the operating parameters, both during and after implementation of the device, by periodic reassessment.

There is, therefore, a need for a technique to evaluate in a simple, rapid, automated, and precise manner, the impact that different CRT therapy operating parameters, including AV and VV delays, so as to optimize the hemodynamic status of a patient.

EP 1736203 A1 and its counterpart U.S. Pat. No. 7,664,547 (both assigned to Sorin CRM, previously known as ELA Medical) describe a CRT device that uses, among other parameters, endocardial acceleration (EA) to determine an optimal pacing configuration at or subsequent to the time of implantation. The endocardial acceleration is measured by an accelerometer integrated in an endocardial lead; for example, as described in EP 0515319 A1 and its counterpart U.S. Pat. No. 5,304,208 (both assigned to Sorin Biomedica Cardio SpA)

Several clinical studies have shown that the endocardial acceleration parameter very accurately and in real time reflects the phenomena related to movements of the heart chamber. It provides comprehensive information on the patient's cardiac mechanics, both during normal operation and poor functioning.

Specifically, EP 1736203 A1 and U.S. Pat. No. 7,664,547, cited above, propose to establish a characteristic relationship between a peak endocardial acceleration ("PEA") and the AVD for each stimulation configuration selected, by scanning the atrioventricular delay AVD and by recording the variations in the amplitude of peak of endocardial acceleration (PEA), usually the first peak of PEA, i.e., PEA1. This characteristic relationship is determined periodically in a test mode triggered by the implantable device, and the results are processed and combined to give a composite performance index that reflects the effectiveness of the configuration. The different characteristics, more specifically the corresponding indices, are evaluated, and the configuration that maximizes this index (optimal performance index) is chosen. This performance index is derived from the area comprised under the PEA vs. AVD characteristic, and corresponds to the efficiency of the ventricular function.

Another optimization method is described in the article by J M Dupuis, et al.: *Programming Optimal Atrioventricular Delay in Dual Chamber Pacing Using Peak Endocardial Acceleration: Comparison with a Standard Echocardiographic Procedure*, PACE 2003, 26: [Pt II], 210-213. This technique also describes scanning of the AVD in the considered stimulation configuration to create a PEA vs. AVD characteristic, but the value that leads to the optimal of the AVD is the inflection point of the characteristic. The inflection point corresponds to a period of maximum filling of the ventricle without truncation of the A wave (a minimum delay between the closing of the mitral valve and the beginning of the QRS complex). The corresponding algorithm, although it gives satisfactory results, suffers from requiring several minutes for execution because multiple scans of AVD are required for various VVD values that are separately tested, before the optimal pair {AVD, VVD} is selected.

Another technique, described in U.S. Pat. Pub. No. 2007/0179542 A1 (Medtronic, Inc.) seeks a correlation or a synchronization between the morphologies of the respective EA and intracardiac electrogram (EGM) signals that respectively reflect mechanical (EA) and electrical (EGM) parameters. The analysis of these signals provides an assumed optimal AVD value for a given configuration of stimulation. But the optimization of the VVD parameter requires successive testing of many different configurations and analysis of the obtained results.

OBJECT AND SUMMARY

It is, therefore, an object of the present invention to provide an improved optimization of the AVD and VVD parameters. It is yet another object to provide a simple, rapid, automated, and precise procedure to simultaneously optimize both AVD and VVD parameters, despite the interdependent nature of these two parameters.

It is yet another object of the present invention to overcome the step of scanning the AVD for each possible stimulation configuration, thus to eliminate a assessment and analysis procedure for each possible VVD for a given AVD that is inherently long given the large number of cardiac cycles required to collect a sufficient number of measurement points.

Broadly, the present invention is directed to operating jointly two different characteristics of the same EA signal to optimize the pair of operating parameters {AVD, VVD}.

As explained in more detail below, during a single cardiac cycle, the EA signal shape presents several peaks corresponding to the main noises that are recognized during each cycle of a healthy heart. The present technique is based on the simultaneous analysis of (i) the EA signal component called EA1 that is linked to the first peak of endocardial acceleration PEA1 and closely correlated to the changes in pressure in the ventricle, and (ii) the EA signal component EA4 that has a much lower amplitude than PEA 1 and is linked to the fourth peak of endocardial acceleration PEA4 and directly correlated to the atrial contraction. This analysis leads to consider:
 the optimization of the AVD by optimizing the moment of onset of the EA4 component, so that ventricular stimulation can take place as late as possible without cutting off the detection of a spontaneous atrial A wave, and
 the optimization of the VVD by optimizing the magnitude of the EA1 component (represented mainly by the peak amplitude or by the energy of the EA1 component), both ventricular stimulation pulses being delivered with the interval (positive or negative) providing the highest stroke volume.

The present technique proposes to combine:
 (i) the measure of a temporal parameter (i.e., the moment of onset) associated with the EA4 component, and
 (ii) the measure of a non-temporal parameter (i.e., amplitude or energy) associated with the EA1 component.
to determine an optimal pair {AVD, VVD} for each stimulation configuration. For each VVD, there is a single optimal value of the AVD, and this optimal pair is dependent upon the selected configuration.

More preferably, the present invention concerns an improvement to an active implanted medical device disclosed in EP 1736203 A1 and its counterpart U.S. Pat. No. 7,664,547 and comprises means for detecting atrial and ventricular events, means for stimulating the right and left ventricles, means for determining an atrioventricular delay AVD measured from the detection of a spontaneous atrial event, or a stimulated atrial event in the absence of a spontaneous ventricular event after a right ventricular pacing is applied, means for calculating an inter-ventricular delay VVD to be applied between the respective moments of stimulation of the right and left ventricles, and means for collecting an endocardial acceleration signal EA representative of the movements produced by the cyclic contractions of the atrial and ventricular cavities.

In accordance with the present invention, the means for calculating the AVD and the VVD includes: means for recognizing and isolating in the EA signal, a component EA4 corresponding to the fourth peak of endocardial acceleration associated with the atrial activity, means for measuring a temporal parameter related to the time interval between the detection of an atrial event and a marker related to the EA4 component immediately following, means for recognizing and isolating in the EA signal a component EA1 that corresponds to the first peak of endocardial acceleration associated with the ventricular isovolumetric contraction, means for measuring a non-temporal parameter related to either the peak amplitude PEA1 or the energy of the EA1 component of the signal, means for determining an optimal AVD ("AVDO") as a function of said temporal parameter related to the EA4 component, said AVDO value being calculated for each of a plurality of different values of VVD, so as to thus obtain a plurality of pairs of values (AVDO, VVD), and means for selecting, among said plurality of pairs of values (AVDO, VVD), one of these pairs of values based on said non-temporal parameter related to the EA1 component.

The means for selecting one of the pairs of values (AVDO, VVD) may select the pair that maximizes the amplitude of the first peak of endocardial acceleration or, respectively, the energy of the EA1 component.

The means for determining the AVDO may include means for calculating the AVDO from said time interval, increased by a delay compensation constant, as described herein below.

The marker linked to the EA4 component may be a marker of the instant of occurrence of the fourth peak of endocardial acceleration, or a marker of the instant of beginning or end of the EA4 component.

In a preferred embodiment, the means for determining the AVDO comprises means, for each value of said plurality of different values of VVD: on a first cardiac cycle, for selecting at least one predetermined AVD value, at least one measurement of said temporal parameter related to the EA4 component, and at least one determination of a corresponding value of AVDO, and means, on the immediately subsequent cardiac cycle, for selecting an AVD value corresponding to the AVDO value determined in the previous cycle, and measuring said non temporal parameter related to the EA1 component.

The predetermined AVD value may be a long value, i.e., a value chosen to be long enough to ensure a detection of a consecutive spontaneous ventricular depolarization.

A plurality of predetermined AVD values may be selected during successive cycles. The temporal parameter associated with the EA4 component is measured with a value of AVD for which the EA4 component can be recognized and isolated.

BRIEF DESCRIPTION OF THE DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements and in which.

DETAILED DESCRIPTION

With reference to FIGS. 1-6, preferred embodiments of the present invention will now be described.

Preliminarily, as regards its software aspects, the present invention can be implemented by an appropriate programming of the software controlling a known device, for example, a microprocessor-based cardiac pacemaker or defibrillator/cardioverter, having hardware circuits, including memory devices, for collecting signals provided by endocardial leads and/or one or more sensors implanted in the patient. These devices include programmable microprocessor circuitry to receive, format, condition, and process electrical signals collected (detected) by implanted electrodes, and deliver stimulation pulses to these electrodes to stimulate the myocardium. It is possible to transmit software instructions by telemetry. The software instructions are stored in a memory of the implantable device and executed to implement the functions of the present invention as is described herein.

The present invention may particularly be applied to implantable devices such as those of the Paradym CRT device family, produced and marketed by Sorin CRM, Clamart France, formerly known as ELA Medical of Montrouge, France. The adaptation of these known devices to implement the functions and features of the present invention is believed to be within the abilities of a person of ordinary skill in the art, therefore it will not be described in detail.

Figure 1:
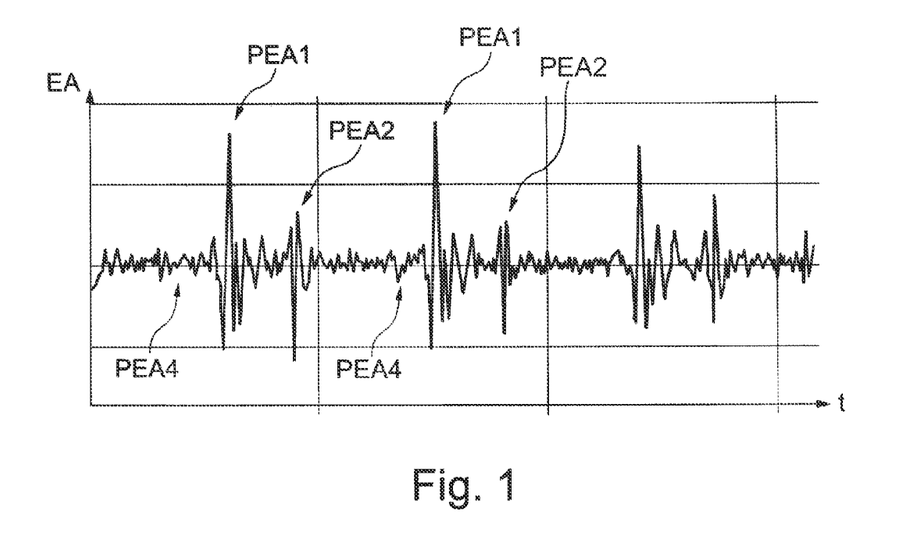
FIG. 1 is a timing diagram showing variations of the endocardial acceleration EA during three successive cardiac cycles.

FIG. 1 illustrates a representative example of an endocardial acceleration signal (EA) collected during three successive cardiac cycles. The EA signal presents two main peaks PEA1 and PEA2 that correspond to the two major noises (i.e., sounds S1 and S2 of the phonocardiogram) recognized in each cardiac cycle. The first peak PEA1 has variations closely linked to the changes of pressure in the ventricle. The peak amplitude PEA1 is more specifically correlated with the pressure change positive maximum dP/dt in the left ventricle. The second peak PEA2 has variations corresponding to the isovolumetric phase of ventricular relaxation. The peak amplitude PEA2 is produced by the sudden deceleration of blood mass in motion in the aorta. Therefore, the EA1 and EA2 components of the EA signal correspond to the two respective endocardial peaks of acceleration PEA1 and PEA2.

The EA signal contains two other components of lower amplitude, referred to as EA3 and EA4, respectively corresponding to the S3 and S4 sounds of the phonocardiogram. The EA4 component that is directly linked to the presence of an atrial contraction particularly presents a PEA4 peak that immediately precedes the PEA1 peak, as shown in FIG. 1. The PEA4 peak is sometimes referred to as "PEA0" to the extent that, from an electrical standpoint, the atrial contraction precedes the ventricular contraction. However, considering the blood flow pumped by the myocardium, the atrial contraction (corresponding to the EA4 component) completes the filling of the ventricle at the end of the diastole (the EA2 component), therefore, from a cardiac hemodynamics point of view, it is designated as "PEA4".

Figure 2:
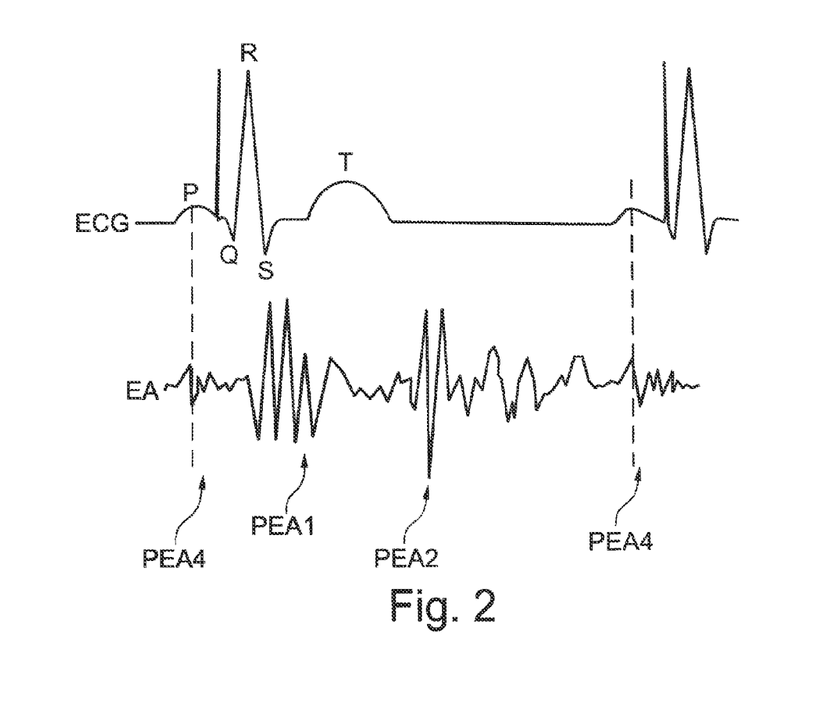
FIG. 2 illustrates various signals characterizing the activity of the heart during a cardiac cycle, including a surface electrocardiogram ECG and the corresponding changes in the endocardial acceleration signal EA.

FIG. 2 illustrates various signals characterizing the activity of the heart during a given cardiac cycle, including a surface electrocardiogram (ECG) signal and the corresponding endocardial acceleration (EA) signal.

The ECG signal contains a P wave that corresponds to the depolarization of the atrium, a QRS complex that corresponds to the ventricular depolarization, and the T wave that corresponds to the ventricular repolarization.

The EA signal, meanwhile, can be decomposed into four components including: the EA4 component that corresponds to the atrial contraction (P wave) followed by the EA1 component that begins after the QRS complex and is caused by a combination of the closure of the atrioventricular valves, the opening of the semilunar valves, and the contraction of the left ventricle. The EA2 component that follows the EA1 component accompanies the end of the ventricular systole and is generated by the closure of the semilunar valves.

Figure 3A:
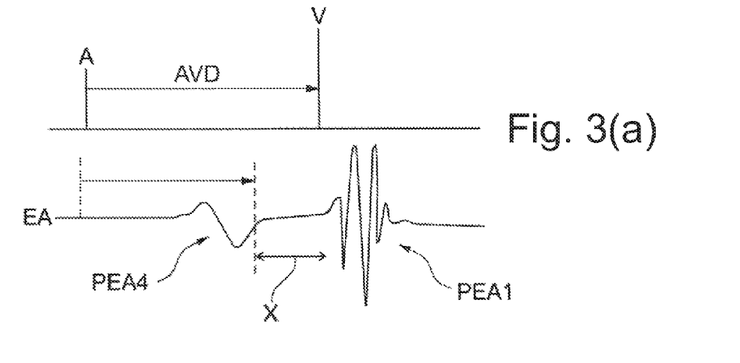
FIGS. 3(a)-3(c) illustrate exemplary EA signals, respectively indicating a long AVD, a proper AVD, and a short AVD.
Figure 3B:
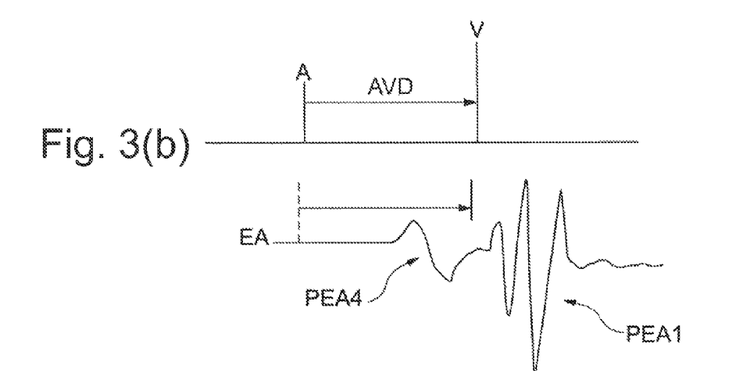
Figure 3C:
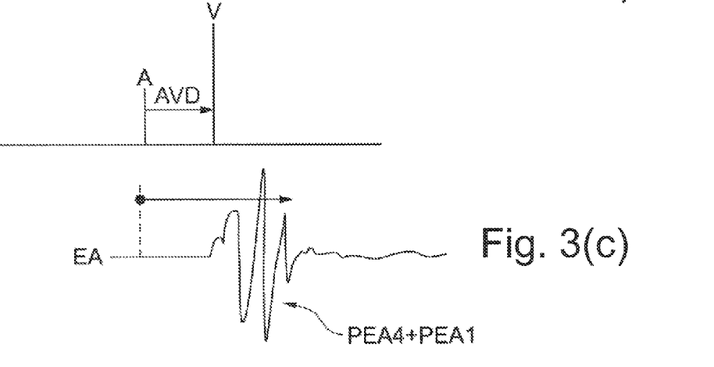

FIGS. 3(a)-3(c) illustrate exemplary EA signals with characteristically different durations of AVD. From the viewpoint of the cardiac mechanics, the AVD must be long enough to allow the atrium to contract and thereby completely empty the blood contained in the atrium into the ventricle, so that ventricular contraction occurs after the atrial contraction has fully taken place. At the same time, the AVD should not occur too long after because the AVD may dissociate the atrium/ventricle system increasing the risk of triggering arrhythmias by retrograde conduction, or reducing the effectiveness of the hemodynamics cardiac cycle. As the atrial contraction ends the ventricular filling, the delay between the end of the ventricular filling and the beginning of the ventricular emptying is a dead time period, i.e., a time that is "lost" from a hemodynamic point of view. In addition, any extended AVD duration impacts the ventricular diastol (specifically the ventricular filling post-emptying) and delays the same timing of the end of the ventricular filling, which is superimposed to the next atrial contraction.

It is therefore important to adapt the AVD as best as possible for each patient, so that the beginning of the ventricular emptying (caused by the stimulation of the ventricle) intervenes immediately after the filling of the ventricle by the atrium.

FIG. 3a illustrates an exemplary EA signal in which the AVD is longer than the optimal value. The long AVD leaves a dead time period X between the end of the atrial contraction (revealed by PEA4) and the beginning of the ventricular contraction. The ventricular contraction results from the V stimulation and produces the PEA1 peak on the EA signal. FIG. 3b shows an exemplary EA signal in which the AVD is either proper or has been adjusted to an optimal value for counteracting the dead time period X to trigger the contraction of the ventricle (V stimulation). The ventricular contraction occurs upon completion of its filling at the end of the atrial contraction that corresponds to the end of the PEA4 peak of the EA signal. FIG. 3c illustrates another exemplary EA signal in which the applied AVD is shorter than the optimal value. In this case, the ventricle begins to contract before it has been completely filled, thereby reducing the ejected volume, and therefore reducing the flow of the heart pump. On the EA signal, this situation is revealed by a merger of the PEA4 peak and the PEA1 peak that immediately follows the PEA4 peak.

Figure 4:
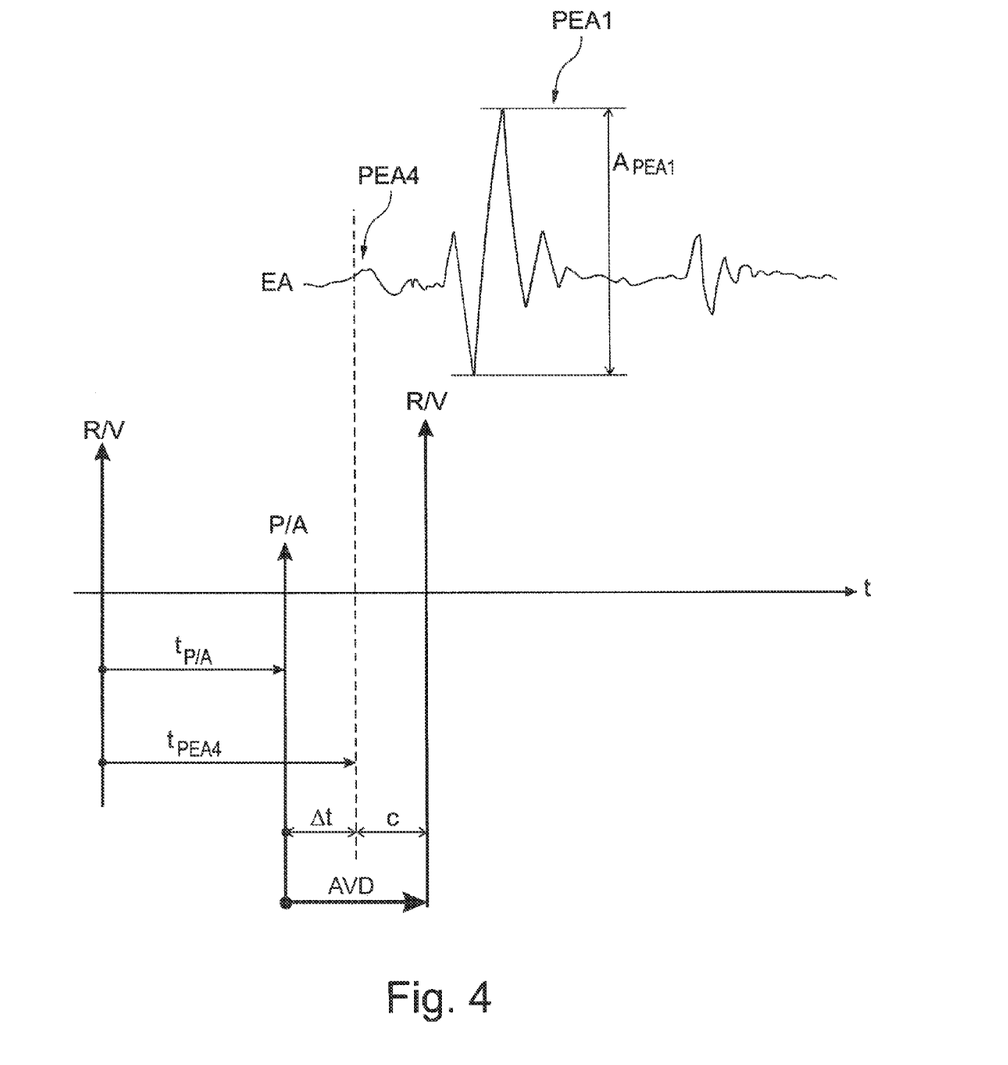
FIG. 4 is a timing diagram of an exemplary EA signal with temporal reference parameters analyzed, according to the present invention.
Figure 5:
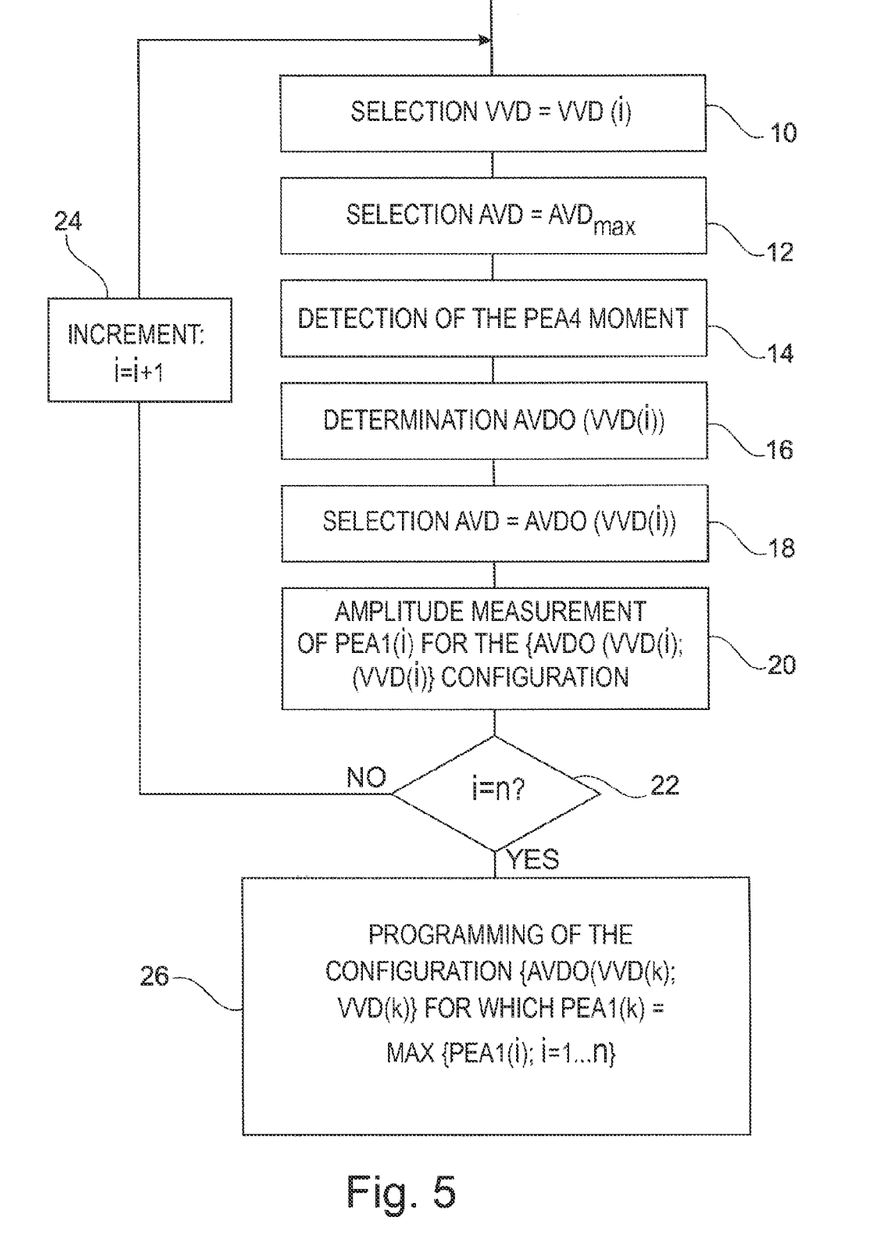
FIG. 5 is a flow chart showing the various stages for optimizing atrioventricular and interventricular delays, implemented by the present invention.

The sequence of implementation of the invention is explained, with reference to FIGS. 4 and 5. FIG. 4 shows exemplary EA signal parameters, and FIG. 5 shows the various stages for optimizing atrioventricular and interventricular delays.

In one embodiment, two parameters of the EA signal are jointly analyzed during a single cardiac cycle, for example:

a temporal parameter related to the EA4 component, to optimize the AVD so that the ventricular pacing occurs as late as possible without cutting off the detection of the A wave or the defection of the EA4 signal component as illustrated in FIG. 3b, and a non-temporal parameter related to the magnitude of the EA1 component (either the PEA1 peak amplitude or the EA1 component energy) to optimize the VVD so that the two ventricular stimulations provide an optimal contractility with maximum ejection volume.

The temporal parameter related to the EA4 component may be determined by a technique, for example, the one described in EP 2092885 A1 and its counterpart U.S. Pat. Pub. No. US2009/0209875 (both assigned to Sorin CRM, previously known as ELA Medical), which are incorporated herein by reference. Temporal markers representative of the occurrence of each of the various components EA1 to EA4 of the EA signal are produced. The temporal markers characterize the peak moment of the analyzed EA component, or a moment of the beginning or of the end of the same component.

In a preferred embodiment, the amplitude of the PEA1 peak, i.e., the maximum peak-to-peak between the positive and negative extremes of the EA1 component of the acceleration signal (marked as $A_{PEA1}$ in FIG. 4) is used for the non-temporal parameter related to the EA1 component. It should be understood, however, that this choice is representative of a preferred embodiment, but is in no way a limitation on the scope of the invention, and other parameters representative the magnitude of the EA1 component can be used, including, for example, the EA signal energy contained in or part of the EA1 component.

The sequence of implementation of the present invention is explained, with reference to FIG. 4 and FIG. 5. After having selected a value VVD(i) for the interventricular delay VVD (block 10 in FIG. 5), the maximum value $AVD_{max}$ of the atrioventricular delay (block 12), usually called the "basic AVD" value provided by the programming the device, is selected. The analysis of the EA4 component involves programming a long AVD to increase the likelihood of detecting a spontaneous ventricular depolarization (R wave).

A characteristic moment of the EA4 component is detected, e.g., the moment of the PEA4 peak (block 14, FIG. 5) by one of the techniques described in the aforementioned EP 2092885 A1 and its U.S. counterpart US2009/0209875.

The moment $t_{PEA4}$ (FIG. 4) of the PEA4 peak is measured by taking as the origin the spontaneous (R) or triggered (V) ventricular event immediately preceding. The instant $t_{P/A}$ of the consecutive spontaneous (P) or triggered (A) atrial event is also measured from the same origin. The Δt difference between these two moments allows, after adding a constant c of compensation, to determine (block 16, FIG. 5) the optimal AVD ("AVDO"), for this tested configuration VVD (i) such that:

$$AVDO(VVD(i))=t_{PEA4}-t_{P/A}+c.$$

The delay compensation constant C is to compensate for the delay between the time $t_{PEA4}$ and the end of the EA4 component.

After the AVD has been established to be the AVDO value determined in the previous step (block 18), the amplitude $A_{PEA1}$ of the PEA1 peak is measured for this same configuration VVD(i) (block 20). The pairs of values {AVDO(VVD(i)); VVD(i)} are determined for all configurations of stimulation VVD(i), i=1 . . . n to be tested (blocks 22, 24). The optimal values of AVD, AVDO, for each configuration, are thus obtained.

The final step (block 26) is to select, among all pairs of values so far determined, the optimal configuration {AVDO(VVD(k)); VVD(k)} that has the highest amplitude of PEA1.

Optionally, to reduce the measurement error, it is possible to calculate average values of AVDO and $A_{PEA1}$, over several cardiac cycles, e.g., 3-5 cycles, preferably over 4 cycles.

Moreover, because the measured parameters of the EA1 and EA4 components depend on the value of the AVD of the previous cycle, the optimization algorithm takes into account the sequence of the atrial-ventricular-atrial events. To this end, the optimization algorithm illustrated in FIG. 5 proceeds, by example, as follows:

programming a long AVD to obtain a spontaneous ventricular contraction;

measuring the $t_{P/A}$ parameter;

programming an AVD shorter than the PR interval (e.g., AVD=PR−40 ms or AVD=30%*PR), to obtain a capture of the V stimulation without a fusion of the EA4 component with other components of the EA signal (this in contrast to the use of the long AVD with spontaneous contraction of the ventricle as illustrated in FIG. 5), and measuring of the $t_{PEA4}$ parameter in a configuration of the V stimulation (instead of a spontaneous contraction of the ventricle as illustrated in FIG. 5).

The optimal AVD, AVDO (VVD(i)) is then determined from these acquired parameters using the corresponding portion of the algorithm described above.

In another embodiment, a plurality of AVD (e.g., AVD=PR−40 ms, AVD=50%*PR and AVD=60 ms) is tested to search for the EA4 component triggered by the atrial contraction (P/A), and the $t_{PEA4}$ parameter is measured to deduce the optimal AVD, AVDO.

On the other hand, in some patients, it is not always possible to clearly distinguish the PEA4 peak because it may be partially merged with the preceding EA2 component (ventricular relaxation) or with the following EA1 component (ventricular contraction). In this case, instead of using the PEA4 peak moment of the EA4 component as the temporal parameter, another temporal parameter such as the starting moment or the ending moment of the EA4 component may be used to calculate the optimal AVD, with an appropriate change to the compensation factor c in the formula given above for calculating the AVDO.

Figure 6A:
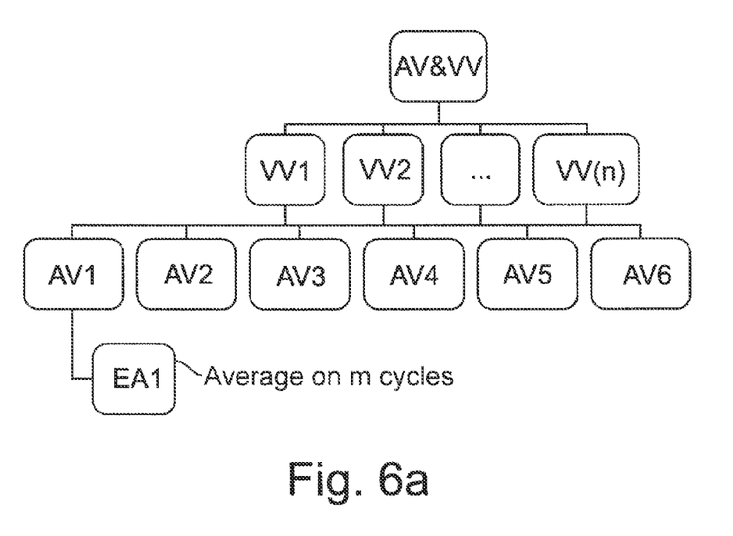
FIG. 6a is a flow chart of a prior art analysis algorithm.
Figure 6B:
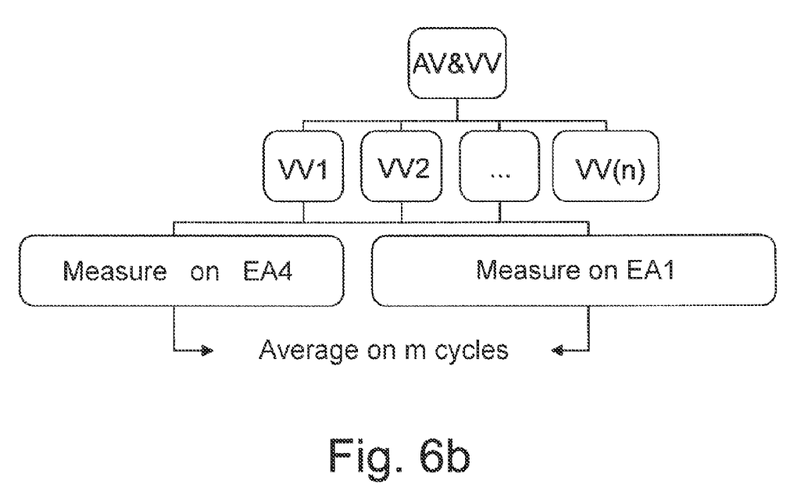
FIG. 6b is a flow chart of an exemplary analysis algorithm implemented in a device, according to the present invention.

FIGS. 6a and 6b illustrate sequencing flowcharts for determining the optimal configuration of the device. FIG. 6a corresponds to a prior art measurement technique based on the calculation of the area with a scanning of the AV delay, as described for example in EP 1736203 A1 and its U.S. counterpart U.S. Pat. No. 7,664,547 cited above. The optimization of the AV and VV delays (first level) involves testing n configurations VV1 . . . VV(n) (second level). For each of these configurations VV(i), the device must perform a scan of the AVD, usually with a minimum of 6 values AV1 . . . AV6 (third level). For each value AV(i) of the AVD in each of the VV(i) configurations, the device measures the amplitude of the PEA1 (or another parameter related to the EA1 component) that is averaged over m cycles (typically, m=4 cycles).

This prior art technique requires n*m*6 cycles to determine the optimal VVD for the n tested VV(i) configurations. Furthermore, at least one cycle of stabilization needs to be added between each change of AVD (not counted in the previous calculation, for simplicity). Finally, the determination of the optimal VVD is followed by the optimization of the optimal AVD in the optimal configuration (VVDO), which requires (m*11) cycles. Therefore, a total of [(n*m*6)+(m*11)] cycles is necessary to obtain the optimum pair (AVDO; VVDO).

FIG. 6b illustrates a flow chart of an exemplary analysis algorithm, according to the present invention. For each configuration VV, the AVD is evaluated without scanning, with a concomitant measure of the temporal parameter related to the EA4 component and the non-temporal parameter related to EA1 component. As explained above, this step requires a minimum of two cycles including one cycle for measuring the two EA parameters (moment of the PEA4 and amplitude of the PEA1) and one stabilization cycle between each change of VVD. If the measurements are averaged over m cycles, the total duration of the test for the n VV(i) configurations is (n*m*2) cycles only, thus saving a considerable time compared to the prior art technique. The present joint analysis technique does not sacrifice the quality of optimization compared to that of the prior art technique.

One skilled in the art will appreciate that the present invention may be practiced by other than the embodiments described above, which are provided for purposes of illustration, and not of limitation.

The invention claimed is:

1. An active implantable medical device for cardiac resynchronization therapy, comprising:

means for detecting spontaneous and stimulated atrial events and spontaneous and stimulated ventricular events;

means for stimulating a patient's left and right ventricles;

means for calculating of an atrioventricular delay (AVD) having a duration counted from a detection of one of a spontaneous and stimulated atrial event;

means for delivering a ventricle stimulation pulse in the right ventricle in the absence of detected spontaneous ventricular event during the calculated AVD;

means for calculating an inter-ventricular delay (VVD) between delivery of stimulation pulses in the patient's left and right ventricles; and means for collecting of an endocardial acceleration (EA) signal representative of movements produced by cyclical contractions of the patient's atrial and ventricular cavities;

wherein the means for calculating the AVD and the means for calculating the VVD further comprise:

means for identifying and isolating in the collected EA signal a component EA4 that corresponds to the fourth peak of the EA signal associated with the atrial activity, and a means for measuring a first measure of a temporal parameter related to the time interval between the atrial event detection and a marker related to the EA4 component that immediately follows the atrial event detection;

means for identifying and isolating in the EA signal a component EA1 that corresponds to the first peak of the EA signal associated with the ventricular isovolumetric contraction, and a means for measuring a second measure of one of a non-temporal parameter related to the peak amplitude or a signal energy of the EA1 component;

means for determining an optimal AVD (AVDO) as a function of said first measure, said AVDO being calculated for each of a plurality of different values of VVD, so as to obtain a plurality of pairs of values {AVDO, VVD} and means for selecting, among said plurality of pairs of values {AVDO, VVD}, one of said pairs of values based on said non-temporal parameter related to the EA1 component.

2. The device of claim 1, wherein the means for selecting one of said pairs of values {AVDO, VVD} further comprises means for selecting said pair of values that maximizes the second measure.

3. The device of claim 1, wherein the means for determining the AVDO further comprises means for calculating the AVDO from said first measure, increased by a delay compensation constant.

4. The device of claim 1, wherein said marker linked to the EA4 component is a marker of a moment of occurrence of the fourth peak of endocardial acceleration.

5. The device of claim 1, wherein said marker linked to the EA4 component is a marker of one of a start time and an end time of the EA4 component.

6. The device of claim 1, wherein said means for determining said AVDO further comprises, for each value of said plurality of different values of VVD, over a first cardiac cycle:
  means for selecting at least one predetermined AVD value;
  means for measuring said temporal parameter related to the EA4 component as said first measure;
  means for determining a corresponding AVDO value as a function of said first measure;
over an immediately following cardiac cycle:
  means for selecting a value corresponding to the AVDO value determined in the previous cycle; and
  means for measuring said one parameter related to the non-temporal EA1 component as said second measure.

7. The device of claim 6, wherein said predetermined AVD value is selected to be long enough to detect a consecutive spontaneous ventricular depolarization.

8. The device of claim 6, wherein a plurality of predetermined AVD values are selected during successive cardiac cycles, and the temporal parameter related to the EA4 component is measured with an AVD value for which the EA4 component is recognized and isolated.

* * * * *